United States Patent [19]
Bagaoisan et al.

[11] Patent Number: 5,480,383
[45] Date of Patent: Jan. 2, 1996

[54] DILATION CATHETER WITH A SMOOTH TRANSITION BETWEEN A STIFF PROXIMAL PORTION AND A FLEXIBLE DISTAL PORTION

[75] Inventors: Celso S. J. Bagaoisan, Union City; Hung V. Ha, San Jose, both of Calif.

[73] Assignee: Advanced Cardiovascular Systems, Inc., Santa Clara, Calif.

[21] Appl. No.: 250,804

[22] Filed: May 27, 1994

[51] Int. Cl.⁶ .................................................. A61M 25/00
[52] U.S. Cl. ............................ 604/96; 604/281; 128/772; 606/194
[58] Field of Search ........................... 604/96, 95, 99, 604/102, 280, 281; 606/192–194; 128/657, 658, 772

[56] References Cited

U.S. PATENT DOCUMENTS

| | | | |
|---|---|---|---|
| 5,047,045 | 9/1991 | Arney et al. | 606/194 |
| 5,100,381 | 3/1992 | Burns | 604/96 |
| 5,120,308 | 6/1992 | Hess | 604/95 |
| 5,171,222 | 12/1992 | Enteneuer et al. | 604/102 |
| 5,238,004 | 8/1993 | Sahatjian et al. | 128/772 |
| 5,259,839 | 11/1993 | Burns | 604/99 |
| 5,334,168 | 8/1994 | Hemmer | 604/281 |
| 5,342,299 | 8/1994 | Snoke et al. | 604/95 |

*Primary Examiner*—John D. Yasko
*Attorney, Agent, or Firm*—Crosby, Heafey, Roach & May

[57] ABSTRACT

A balloon dilatation having a catheter shaft with inner and outer tubular members with the proximal portion of the inner tubular member being formed of a pseudoelastic NiTi alloy having an $A_f$ at or below body temperature. The austenite phase is stable at body temperature exhibits a stress induced transformation, to the martensite phase which has a much lower modulus of elasticity than the austenite phase. The distal portion of the inner tubular member is formed of a flexible plastic material. The junction of the proximal and distal portions of the inner tubular member is preferably supported by a transition sleeve formed of a high strength plastic such as polyimide to provide a smoother transition between the proxima and distal portions of the inner tubular member and in turn the proximal and distal portion of the catheter shaft.

16 Claims, 2 Drawing Sheets

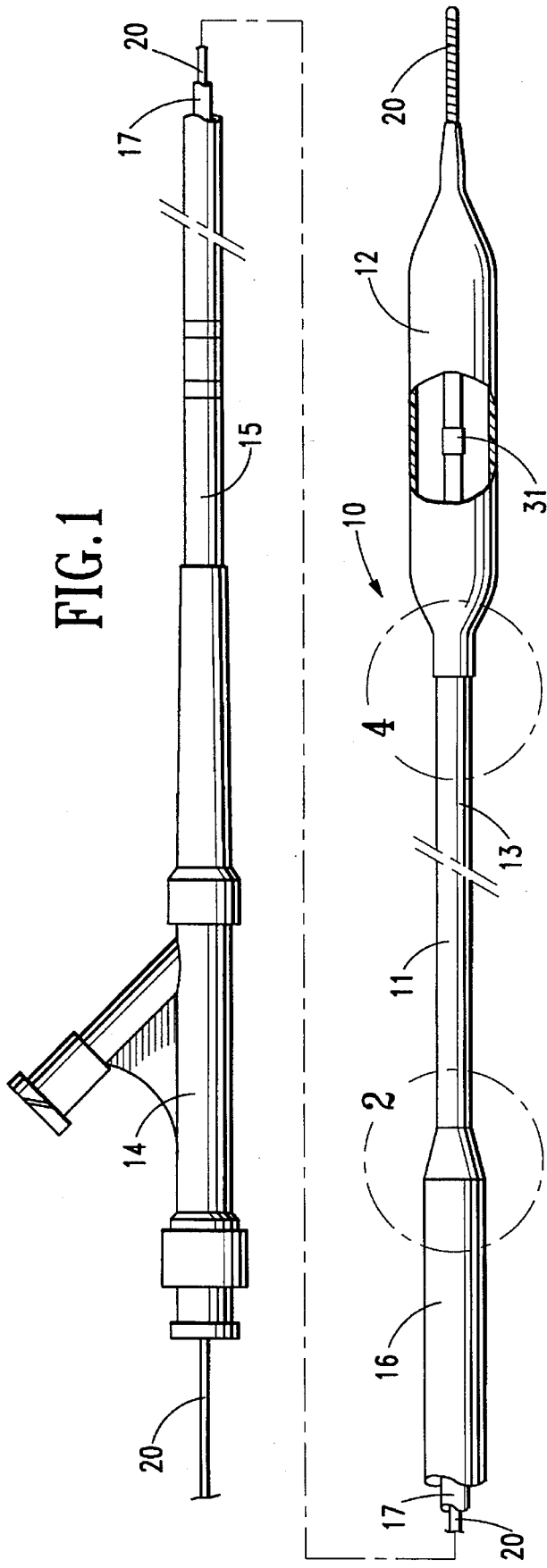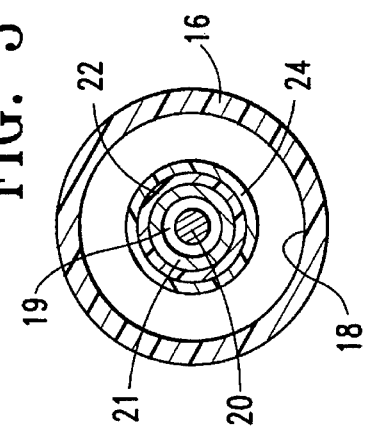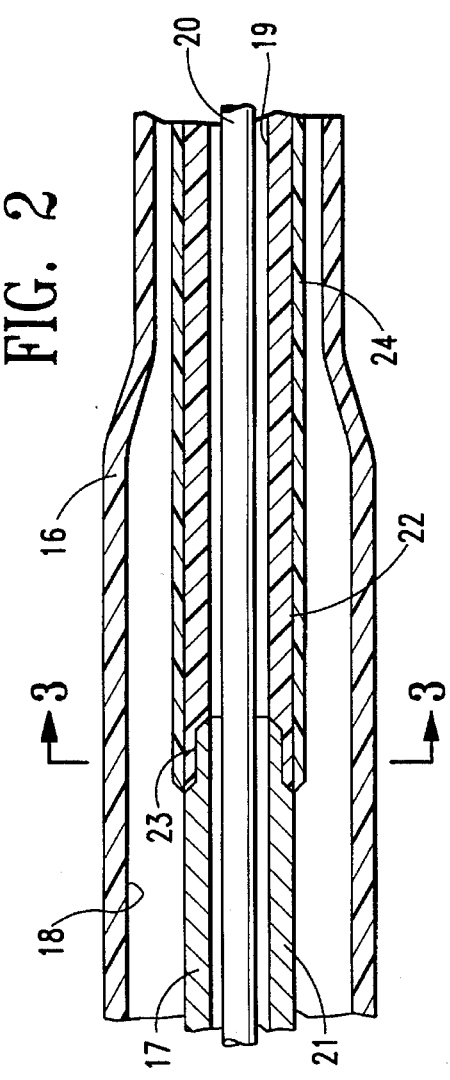

DILATION CATHETER WITH A SMOOTH TRANSITION BETWEEN A STIFF PROXIMAL PORTION AND A FLEXIBLE DISTAL PORTION

BACKGROUND OF THE INVENTION

This invention relates to the field of intravascular catheters, and more particularly to a dilatation catheter for percutaneous transluminal coronary angioplasty (PTCA).

In PTCA procedures a guiding catheter having a preformed distal tip is usually percutaneously introduced into the patient's femoral artery by means of a conventional Seldinger technique and retrogradely advanced therein until the distal portion of the guiding catheter is located within the patient's ascending aorta with distal tip of the guiding catheter seated in the ostium of a desired coronary artery. The proximal end of the guiding catheter is torqued from outside the patient to guide distal tip of the guiding catheter into the desired ostium. A guidewire is positioned within an inner lumen of an dilatation catheter and then both are advanced through the guiding catheter to its distal end. The guidewire is first advanced out of the distal end of the guiding catheter into the patient's coronary artery until the distal end of the guidewire crosses a lesion to be dilated. Then the dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with liquid one or more times to a predetermined size at relatively high pressures (e.g. greater than 4 atmospheres) to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

Commercially available over-the-wire dilatation catheters for angioplasty and other vascular procedures usually comprise an elongated shaft with an inflatable dilatation member on a distal portion of the shaft and an adapter on the proximal end of the shaft for the delivery of inflation fluid through an inner lumen extending through the catheter shaft to the interior of the inflatable dilatation member.

The progression of improvements in dilatation catheters generally has been to make the catheters with lower profiles and with the proximal portions of the catheters being much stiffer than the distal portions. However, this progression has also increased the difficulty in forming smooth transitions between the various sections of the catheter shaft. This is particularly noticeable with catheters having proximal portions formed of metallic tubing such as stainless steel hypotubing.

What has been needed is a dilatation catheter which has a stiff proximal portion for pushability, a very flexible distal portion to facilitate advancement over a guidewire, i.e. trackability, within a patient's coronary anatomy and a smooth transition between the proximal and distal portions. The dilatation catheter of the present invention provides such a combination of such desirably properties.

SUMMARY OF THE INVENTION

This invention is directed to a dilatation catheter which has a relatively stiff proximal shaft portion, a very flexible distal shaft portion and a smooth transition between the proximal and distal portions of the catheter shaft.

The dilatation catheter of the invention generally has an elongated catheter shaft with an inflatable dilatation member on a distal portion of the catheter. The catheter shaft has an outer tubular member and an inner tubular member disposed within the inner lumen of the outer tubular member, with a distal extremity of the inflatable dilatation member sealed about and secured to a distal extremity of the inner tubular member. A proximal extremity of the inflatable dilatation member sealed about and secured to a distal extremity of the outer tubular member or the inflatable dilatation member and the outer tubular member may be formed in a unitary construction from the same material.

In accordance with the invention, the inner tubular member has a proximal portion formed of a NiTi alloy which may either be in a martinsite phase or be in an austenite phase which is readily transformed at body temperature by the application of stress to the martensite phase. The austenite phase should be stable at body temperature (37° C.). The inner tubular member also has a distal portion formed of flexible plastic material such as high density polyethylene or a polymer such as Hytrel® which is available from DuPont. A smooth transition between the proximal and distal portions of the inner tubular member can be maintained by selecting the material to provide a differential in the respective moduli of elasticity of the proximal and distal inner tubular portions to not more than about $12 \times 10^6$ psi and not less than $3.5 \times 10^6$ psi, preferably not more than about $10 \times 10^6$ psi and not less than about $4 \times 10^6$ psi. A NiTi alloy exhibiting pseudoelastic characteristics is preferred because the pseudoelasticity allows the proximal portion of the inner tubular member to readily deform under stress with a phase transformation from the higher modulus of elasticity austenite phase to the lower modulus martensite phase. A suitable pseudoelastic NiTi alloy material is described in copending application Ser. No. 08/071,322, filed on Jun. 2, 1993, now U.S. Pat. No. 5,411,476 which is incorporated herein in its entirety by reference. The modulus of elasticity of the NiTi alloy in the martensite phase is typically about 4 to about $6 \times 10^6$ psi and in the austenite phase is about 8 to about $12 \times 10^6$ psi. The modulus of elasticity of the plastic distal portion is typically about 0.07 to about $0.15 \div 10^6$ psi.

In a presently preferred embodiment of the invention, a supporting transition sleeve is disposed about the junction between the proximal portion and the distal portion of the inner tubular member to provide an even smoother transition. The transition sleeve should have an modulus of elasticity intermediate between the modulus of the NiTi alloy in the proximal portion and the modulus of the plastic material of the distal portion of the inner tubular member. Typically, the modulus of elasticity of the sleeve material should be about 0.2 to about $0.6 \times 10^6$ psi. Suitable high strength polymer materials for the transition sleeve include polyimide, poly(ethylene) terephthalate (PET) and the like which are commercially available. One commercially available polymer is TRAY-TUF 9506 which is a PET.

The dilatation catheter of the invention has excellent pushability due to the stiff proximal portion, yet it has a very flexible distal portion and a very smooth transition between the proximal and distal portions which provides improved tracking over a guidewire, even when the guidewire over which the catheter is advanced is in a positioned with tight curves. These and other advantages of the invention will become more apparent from the following detailed description of the invention and the accompanying exemplary drawings.

BRIEF DESCRIPTION OF THE DRAWINGS

FIG. 1 is an elevational view partially in section of a dilatation catheter assembly with a guidewire therein which embodies features of the invention.

FIG. 2 is an enlarged longitudinal cross-sectional view of the catheter assembly shown in FIG. 1 within the circle 2.

FIG. 3 is an transverse cross-sectional view of the shaft of the catheter assembly shown in FIG. 2 taken along the lines 3—3.

DETAILED DESCRIPTION OF THE INVENTION

Figure 4:
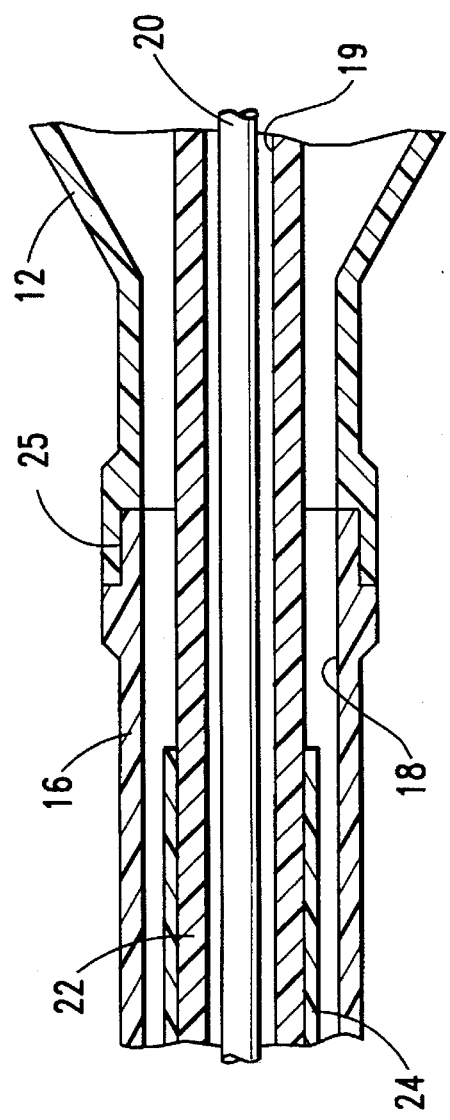
FIG. 4 is an enlarged, longitudinal cross-sectional view of the catheter shaft shown in FIG. 1 within the circle 4.

As shown in FIG. 1 the dilatation catheter 10 of the invention generally includes an elongated catheter shaft 11 with an inflatable dilatation balloon 12 on a distal portion 13 and an adapter 14 mounted on the proximal end of proximal portion 15.

The catheter shaft 11 which is illustrated in more detail in FIGS. 2 and 3, has an outer tubular member 16 which tapers to a smaller diameter in the distal portion 13 of the catheter and an inner tubular member 17 disposed within the outer tubular member and defining with the outer tubular member annular lumen 18 which is in fluid communication with the interior of the inflatable dilatation balloon 12. The inner tubular member 17 has an inner lumen 19 extending therein which is configured to slidably receive a guidewire 20 suitable for advancement through a patient's coronary arteries.

The distal extremity of the inflatable dilatation balloon 12 is sealingly secured to the distal extremity of the inner tubular member 17 and the proximal extremity of the balloon is sealingly secured to the distal extremity of the outer tubular member 16 as shown in FIGS. 1 and 4.

The inner tubular member 17 has a proximal portion 21 formed of a NiTi alloy tube with pseudoelastic characteristics including a stable austenite phase at body temperature, i.e. an $A_f$ at or below body temperature, and the ability to transform to a lower modulus martensite phase upon the application of stress.

As shown in FIG. 2 the distal extremity of the proximal portion 21 of the inner tubular member 17 is secured to the proximal extremity of the distal portion 22 of the inner tubular member at a lap joint 23 formed by suitable means such as heat or laser fusion or commercially available adhesives, e.g. cyanoacrylate adhesives. The distal portion 22 of the inner tubular member 17 is formed of a melt processable polymer material such as Hytrel® and is generally quite flexible in comparison to the proximal portion 21. A transition sleeve 24 is disposed about and secured to the lap joint 23 to provide additional strength and also a smoother transition between the metallic proximal portion 21 and the plastic distal portion 22. This ensures that the distal portion 22 does not kink adjacent to the lap joint 23 when passing through tortuous anatomy.

The junction between the proximal extremity of the balloon 12 and the distal extremity of the outer tubular member 16 which as illustrated in FIG. 4, is a lap joint 25 which may be formed in the same or similar manner as the lap joint 23 between the proximal and distal portions of the inner tubular member 17. The transition sleeve 24 may extend to a location proximal to the lap joint 25 as shown.

Figure 5:
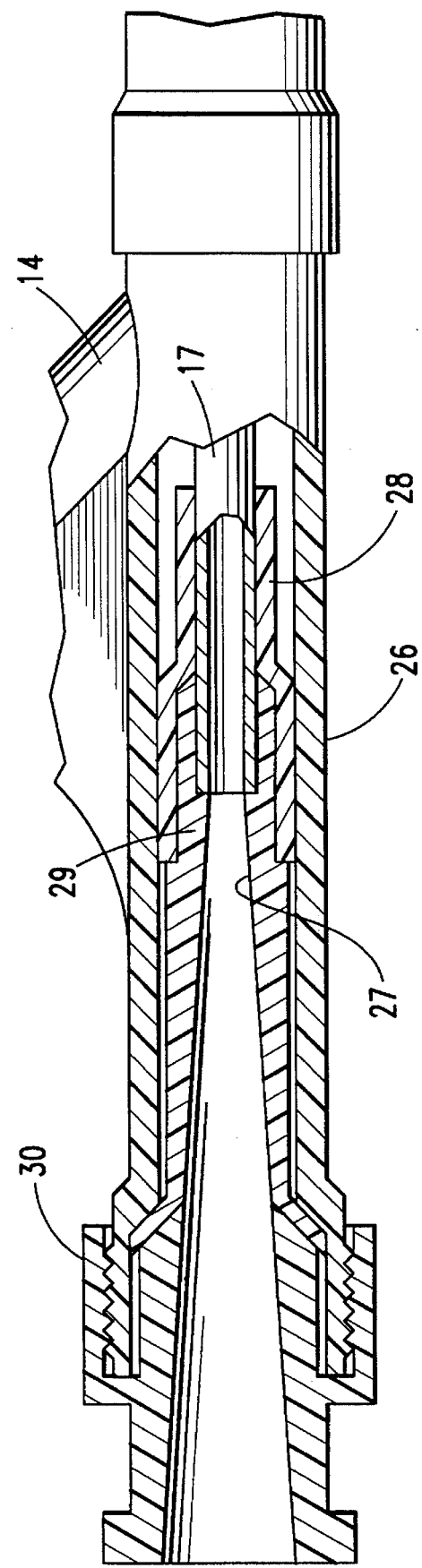
FIG. 5 is an enlarged, longitudinal cross-sectional view of the center arm of the adapter on the proximal end of the dilatation catheter shown in FIG. 1.

The central arm 26 of the adapter 14 is best shown in FIG. 5. The proximal extremity of the inner tubular member 17 is secured within the inner lumen 27 of central arm 26 by means of sealing elements 28 and 29 which are disposed about the proximal extremity and pressed against the exterior thereof by the threaded end cap 30.

The length of the dilatation catheter 10 may be about 90 to about 150 cm in length, typically about 135 cm for PCTA. The outer tubular member 17 has an OD of about 0.03 to about 0.05 inch (0.76–1.27 mm) and an ID of about 0.020 to about 0.035 inch (0.508–0.899 mm). The outer tubular member 17 may taper in its distal portion to a smaller OD of about 0.04 to about 0.02 inch (1.02–10.5 mm) and a smaller ID of about 0.03 to about 0.015 inch ((0.762–0.381 mm). The smaller diameter portion between the taper and the proximal extremity of the balloon 12 may be about 5 to about 15 cm in length.

The inner tubular member 17 has an OD ranging from about 0.014 to about 0.026 inch (0.356–0.66 mm). The ID of the inner tubular member 18 will be usually determined by the diameter of the guidewire which is to be used with the catheter, which may range from about 0.008 to about 0.02 inch ((0.203–0.51 mm). The diameter of the inner lumen should be about 0.002 to about 0.005 (0.051–0.127 mm) inch larger than the OD of the guidewire to be used. Usually there will be a family of catheters for each size of guidewire with a variety of maximum inflated balloon sizes, e.g. 0.5 to about 4 mm in diameter and with various working lengths ranging from about 2 to about 20 cm.

The NiTi alloy from which the proximal portion 12 of the inner tubular member 17 consists essentially of about 30 to about 52% titanium and the balance nickel and up to about 10% of one or more additional alloying elements. The additional alloying elements may be selected from the group consisting of up to 3% each of iron, cobalt, chromium, platinum and palladium and up to about 10% copper and vanadium. Generally, the nickel level should be at least about 38%, but not more than about 52% because at nickel levels above about 52% the alloy becomes too brittle to fabricate by cold working. As used herein all references to percent alloy compositions for NiTi alloy are atomic percent unless otherwise noted.

To form the elongated pseudoelastic proximal portion of the inner tubular member, tubular stock of the preferred alloy material is first thermomechanically processed through a series of steps including cold working and inter-annealing at temperatures between about 600° to about 800° C. for about 5 to about 30 minutes and then given a final cold working, preferably by drawing, to effect a final size reduction of about 10% up to about 75% in the transverse cross section thereof, preferably about 10% to about 40%. After the final cold working step, the NiTi tubular material is given a heat treatment at a temperature of about 350° to about 600° C. for about 0.5 to about 60 minutes to generate the pseudoelastic characteristics. To impart a straight memory, the cold worked material may be subjected to a longitudinal stress equal to about 5% to about 50%, preferably about 10% to about 30%, of the yield stress of the material (as measured at room temperature) during a heat treatment of about 350° to about 600° C. This thermomechanical processing provides a relatively uniform residual stress in the tubular NiTi material. For an even greater degree of straightness, the cold worked tubular NiTi material may be given a mechanically straightening before the heat treating at temperatures between about 350° to about 600° C., preferably about 450° to about 525° C. The latter treatment provides substantially improved one-to-one torque response. The cold worked, straightened and heat treated tubular NiTi alloy material has an austenite finish transformation temperature ($A_f$) generally of about −20° to about 40° C. and usually less than body temperature (approx. 37° C.). It is preferred to fully anneal the tubular stock prior to cold working so that the material will always have the same metallurgical structure at the start of the cold working to provide consistent final properties and to ensure adequate ductility for cold working. It will be appreciated by those skilled in the art that the alloy can be cold worked in a variety of ways other than drawing, such as rolling or swaging. The ultimate tensile strength of the cold worked and heat treated product is well above 150 ksi (1034M Pa) with an ultimate elongation at failure of about 12 to about 18% and a modulus of elasticity of about 8–12×10$^6$psi.

The proximal portion of the inner tubular member formed of a pseudoelastic alloy has a stable austenite phase at body temperature which will transform to martensite phase upon the application of stress and will exhibit a recoverable strain of at least about 4% upon the stress induced transformation of the austenite phase to the martensite phase. The onset of the stress induced phase change from austenite to martensite, preferably begins when the specimen has been strained about 2% and extends to a strain level of about 8% at the completion of the phase change. The stress and strain referred to herein is measured by tensile testing. The stress-strain relationship determined by applying a bending moment to a cantilevered specimen is slightly different from the relationship determined by tensile testing because the stresses which occur in the specimen during bending are not as uniform as they are in tensile testing. The rate of stress change during the phase transformation is much less than the rate of stress change either before or after the stress-induced transformation. In some instances the stress level during the phase change is almost constant.

To the extent not previously described herein, the various catheter components may be formed of conventional materials. For example, the outer tubular member 17 may be formed of high density polyethylene, the radiopaque marker 31 may be a gold band, the adapter body may be formed of polycarbonate polymers, the sealing members 28 and 29 may be elastomeric or latex in composition. The balloon 12 may be a relatively inelastic high strength material such as polyethylene, polyethylene terephthalate, polyolephinic ionomers such as Surlyn®, nylon and the like which are frequently used to form dilatation balloons. As previously mentioned the balloon and the outer tubular member may be formed from the same tubing.

While the present invention has been described herein in terms of certain preferred embodiments wherein the tubular member having a high modulus proximal portion and a low modulins distal portion is an inner tubular member. Those skilled in the art will recognize that modifications and improvements may be made to the invention. For example, a tubular member with a high modulus proximal portion and a low modulus distal portion may be used as the outer tubular member of the dilatation catheter. Other modifications may be made with out departing from the scope thereof.

What is claimed is:

1. A dilatation catheter for performing angioplasty procedures within a patient's artery, comprising:
   a) an outer tubular member having proximal and distal ends and an inner lumen extending therein;
   b) an inner tubular member disposed within the inner lumen of the outer tubular member which has an inner lumen extending therein;
      a proximal portion formed of a NiTi alloy having a desired modulus of elasticity;
      a distal portion formed of a flexible plastic material having a much lower modulus of elasticity than the modulus of elasticity of the NiTi alloy;
      a transition sleeve having a modulus of elasticity between the modulus of the NiTi alloy and the modulus of the plastic material of the distal portion and supporting a distal extremity of the proximal portion and a proximal extremity of the distal portion; and
   c) an inflatable dilatation member on a distal portion of the catheter with a distal extremity secured to the distal extremity of the inner tubular member.

2. The dilatation catheter of claim 1 wherein the modulus of elasticity of the NiTi alloy is about 4 to about 12×10$^6$ psi.

3. The dilatation catheter of claim 1 wherein the modulus of elasticity of the NiTi alloy in the martensite phase is about 4 to about 6× 10$^6$ psi.

4. The dilatation catheter of claim 1 wherein the NiTi alloy is pseudoelastic and exists in a stable austenite phase at body temperature.

5. The dilatation catheter of claim 1 wherein the modulus of elasticity of the NiTi alloy in the austenite phase is about 8 to about 12×10$^6$ psi.

6. The dilatation catheter of claim 1 wherein the plastic distal portion has a modulus of elasticity of about 0.07 to about 0.15×10$^6$ psi.

7. The dilatation catheter of claim 1 wherein the transition sleeve has a modulus of elasticity of about 0.2 to about 0.6×10$^6$ psi.

8. The dilatation catheter of claim 1 wherein the transition sleeve is formed of polyimide.

9. The dilatation catheter of claim 1 wherein the transition sleeve is formed of poly(ethylene) terephthalate.

10. The dilatation catheter of claim 1 wherein the differential between the modulus of elasticity of the proximal portion of the inner tubular member and the modulus of elasticity of the distal portion of the inner tubular member is at least 3.5×10$^6$ psi but not more than 12×10$^6$ psi, 11. The dilatation catheter of claim 1 wherein the outer tubular member tapers from a first diameter to a second smaller diameter at a location distal to the proximal portion of the inner tubular member.

12. The dilatation catheter of claim 1 wherein the transition sleeve extends distally at least about 5 cm from the distal end of the proximal portion of the inner tubular member.

13. The dilatation catheter of claim 1 wherein the proximal end of the distal portion of the inner tubular member extends over the distal end of the proximal portion in a lap joint.

14. The dilatation catheter of claim 13 wherein the transition sleeve extends proximally over the proximal extremity of the distal portion of the inner tubular member which overlaps the distal extremity of the proximal portion in the lap joint.

15. A dilatation catheter for performing angioplasty procedures within a patient's artery, comprising:
   a) an outer tubular member having proximal and distal ends and an inner lumen extending therein;
   b) an inner tubular member disposed within the inner lumen of the outer tubular member which has an inner lumen extending therein;
      a distal portion formed of a flexible plastic material having a desired modulus of elasticity;
      a proximal portion formed of a NiTi alloy having a modulus of elasticity not less than about 3.5×10$^6$ psi but not more than 12×10$^6$ psi greater than the modulus of the flexible plastic material; and c) an inflatable dilatation member on a distal portion of the catheter with a distal extremity secured to the distal extremity of the inner tubular member.

16. In a dilatation catheter for performing an angioplasty procedure within a patient's artery having a catheter shaft and a dilatation balloon on a distal portion thereof, the improvement in the catheter shaft which includes a tubular member having an inner lumen extending therein;

a proximal portion formed of a NiTi alloy having a desired modulus of elasticity;

a distal portion formed of a flexible plastic material having a much lower modulus of elasticity than the modulus of elasticity of the NiTi alloy; and a transition sleeve having a modulus of elasticity between the modulus of the NiTi alloy and the modulus of the plastic material of the distal portion which is disposed about and supports a distal extremity of the proximal portion and a proximal extremity of the distal portion.

* * * * *